US010195005B2

(12) United States Patent
Wallström et al.

(10) Patent No.: US 10,195,005 B2
(45) Date of Patent: Feb. 5, 2019

(54) INTERDENTAL CLEANER

(71) Applicant: TePe Munhygienprodukter AB, Malmö (SE)

(72) Inventors: Paul Wallström, Limhamn (SE); Jan-Inge Larsson, Veberöd (SE); Alexander Dingizian, Malmö (SE)

(73) Assignee: TePe Munhygienprodukter AB, Malmö (SE)

( * ) Notice: Subject to any disclaimer, the term of this patent is extended or adjusted under 35 U.S.C. 154(b) by 0 days.

(21) Appl. No.: 15/122,137

(22) PCT Filed: Dec. 17, 2014

(86) PCT No.: PCT/EP2014/078338
§ 371 (c)(1),
(2) Date: Aug. 26, 2016

(87) PCT Pub. No.: WO2015/011299
PCT Pub. Date: Jan. 29, 2015

(65) Prior Publication Data
US 2016/0367345 A1    Dec. 22, 2016

(30) Foreign Application Priority Data

Mar. 6, 2014  (EP) .................................... 14158195

(51) Int. Cl.
*A61C 15/00* (2006.01)
*A61C 15/02* (2006.01)
*A46B 9/00* (2006.01)

(52) U.S. Cl.
CPC .............. *A61C 15/02* (2013.01); *A46B 9/005* (2013.01); *A46B 2200/108* (2013.01)

(58) Field of Classification Search
CPC ........ A61D 15/02; A61D 15/046; A46B 9/05; A46B 2200/108; A45D 40/262
See application file for complete search history.

(56) References Cited

U.S. PATENT DOCUMENTS

| 1,746,591 A | 2/1930 | Heymann et al. |
| 3,775,848 A | 12/1973 | Barnett |
| 4,832,061 A | 5/1989 | Hwang |
| 4,922,936 A | 5/1990 | Buzzi et al. |
| 5,040,260 A | 8/1991 | Michaels |
| 5,283,924 A | 2/1994 | Kaminski et al. |

(Continued)

FOREIGN PATENT DOCUMENTS

| CN | 201085230 Y | 7/2008 |
| CN | 201790907 U | 4/2011 |

(Continued)

OTHER PUBLICATIONS

Hopff, Heinrich, "Grundriss der organischen Cheme", Munchen 1952, p. 130.

(Continued)

*Primary Examiner* — Rachel R Steitz
(74) *Attorney, Agent, or Firm* — Lowe Graham Jones

(57) ABSTRACT

An interdental cleaner has a gripping portion (3) and a cleaning portion (4) formed by an elongate body made from a thermoplastic material. The cleaning portion (4) has a coating made of a self-adhesive, heat-vulcanized rubber material forming peripheral, flexible brush members (6).

27 Claims, 9 Drawing Sheets

(56) References Cited

U.S. PATENT DOCUMENTS

| | | |
|---|---|---|
| 5,527,181 A | 6/1996 | Rewis et al. |
| 5,775,346 A * | 7/1998 | Szyszkowski ......... A61C 15/00 132/321 |
| 6,085,761 A | 7/2000 | Inaba |
| 6,158,444 A | 12/2000 | Weihrauch |
| 6,767,209 B1 | 7/2004 | Tomita et al. |
| 6,891,869 B2 | 5/2005 | Augusto |
| D521,737 S | 5/2006 | Siemer |
| D575,004 S | 8/2008 | Jansheski et al. |
| D592,916 S | 5/2009 | Mazzetta et al. |
| D622,557 S | 8/2010 | Kerulis et al. |
| D687,682 S | 8/2013 | Tsioukis |
| 8,528,147 B2 | 9/2013 | Larsson et al. |
| 9,226,802 B2 | 1/2016 | McCafferty et al. |
| 9,642,682 B2 | 5/2017 | Kato |
| 2008/0307596 A1 | 12/2008 | Hohlbein |
| 2010/0015567 A1 | 1/2010 | Elbaz et al. |
| 2010/0024839 A1 | 2/2010 | Kalbfeld et al. |
| 2011/0041271 A1 | 2/2011 | Huang |
| 2011/0067725 A1 | 3/2011 | Manici |
| 2013/0340184 A1 | 12/2013 | Fritsch |
| 2014/0008837 A1 | 1/2014 | Eatherton |
| 2014/0158152 A1 | 6/2014 | Butz et al. |
| 2014/0166043 A1 | 6/2014 | Dishon |
| 2014/0178650 A1 | 6/2014 | Schnurr |
| 2015/0114428 A1 | 4/2015 | Kato |
| 2015/0282601 A1 | 10/2015 | Butz et al. |
| 2015/0335141 A1 | 11/2015 | Schar et al. |
| 2016/0058531 A1 | 3/2016 | Adriano et al. |

FOREIGN PATENT DOCUMENTS

| | | |
|---|---|---|
| CN | 102088888 A | 6/2011 |
| DE | 68916949 | 3/1995 |
| DE | 202009009283 | 10/2009 |
| DE | 4020110008310017 | 6/2011 |
| DE | 4020110008310019 | 6/2011 |
| EP | 0 153 011 A1 | 8/1985 |
| EP | 0161057 | 11/1985 |
| EP | 0202296 | 1/1989 |
| EP | 0707836 | 4/1996 |
| FR | 930114 | 4/1993 |
| JP | 54-170098 U | 12/1979 |
| JP | 1979-170098 U | 12/1979 |
| JP | 5-93416 | 12/1993 |
| JP | 2004041260 A | 2/2004 |
| JP | 2004209242 A | 7/2004 |
| JP | 2012024216 A | 2/2012 |
| JP | 2012095868 A | 5/2012 |
| JP | 2012152928 A | 8/2012 |
| JP | 2013188299 A | 9/2013 |
| JP | 2013192866 A | 9/2013 |
| SU | 1811389 A3 | 4/1993 |
| WO | 8706452 | 11/1987 |
| WO | 9204935 | 4/1992 |
| WO | 9816169 A1 | 4/1998 |
| WO | 2004004515 A1 | 1/2004 |
| WO | 2009150964 A1 | 12/2009 |
| WO | 2012110226 A1 | 8/2012 |
| WO | 2012156025 A1 | 11/2012 |
| WO | 2013176297 A1 | 11/2013 |
| WO | 2014005659 A1 | 1/2014 |
| WO | 2014023395 A1 | 2/2014 |
| WO | 2014023424 | 2/2014 |
| WO | 2014023424 A1 | 2/2014 |

OTHER PUBLICATIONS

Hopff, Heinrich, "Grundriss der organischen Cheme", Munchen 1952, 2 Pages.

* cited by examiner

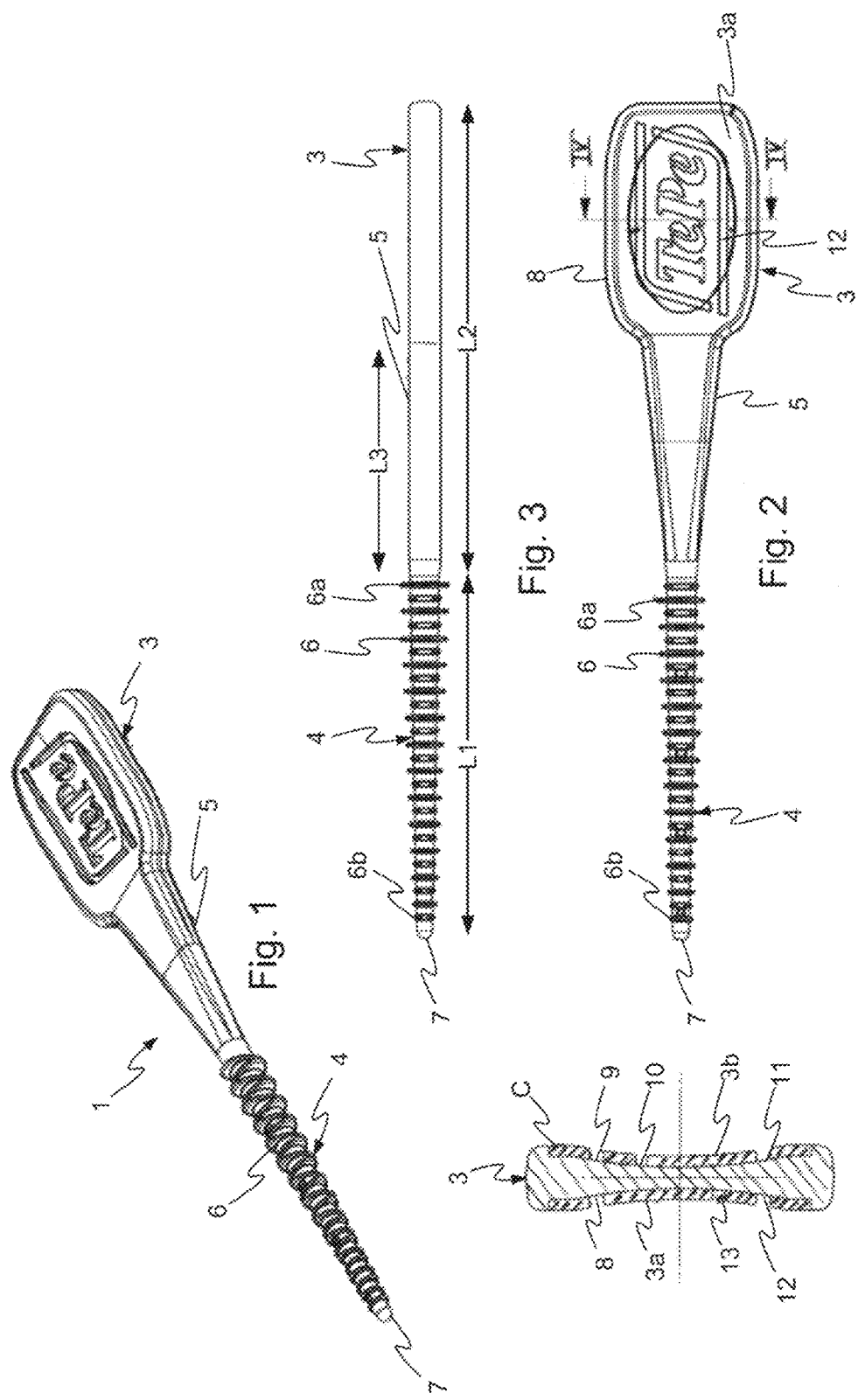

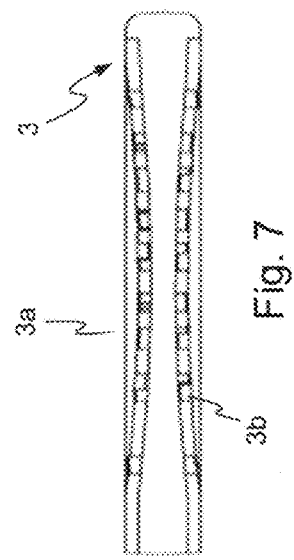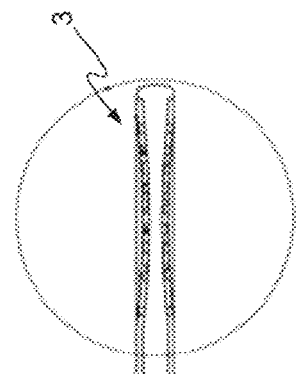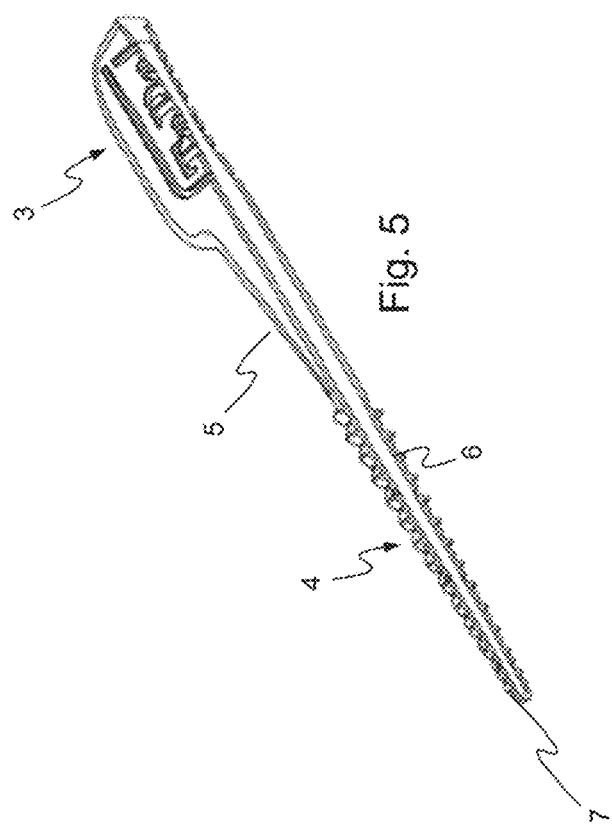

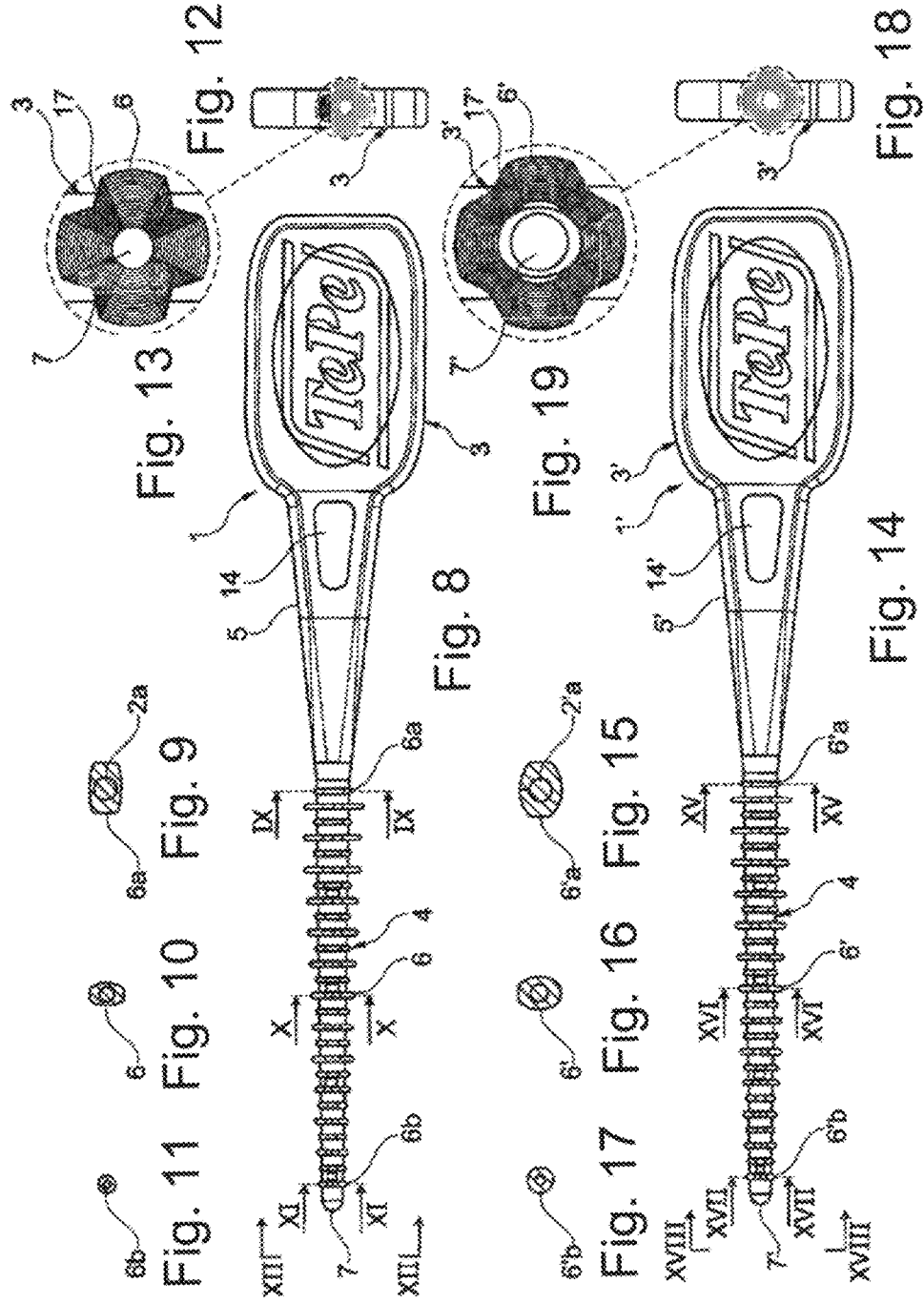

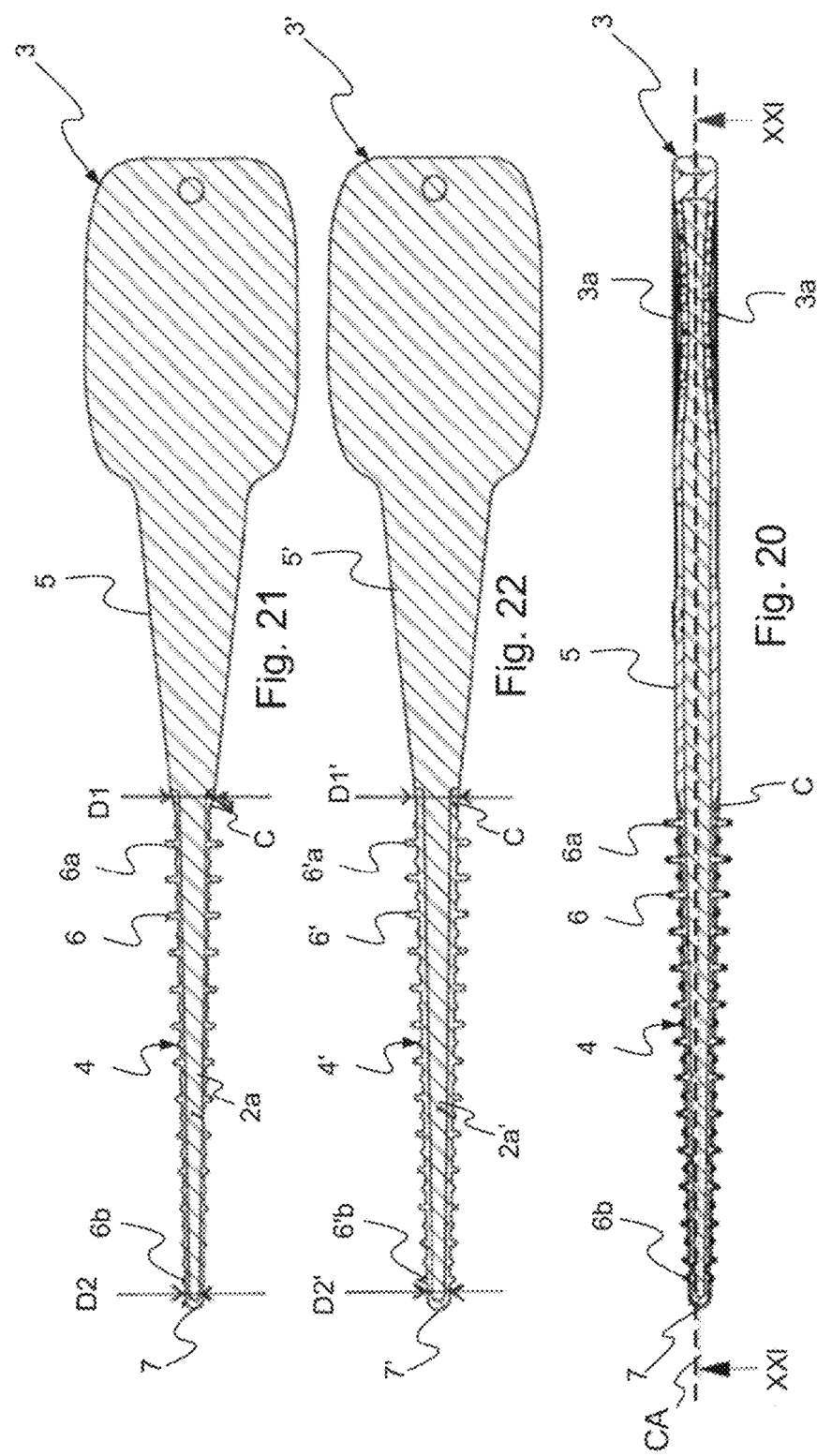

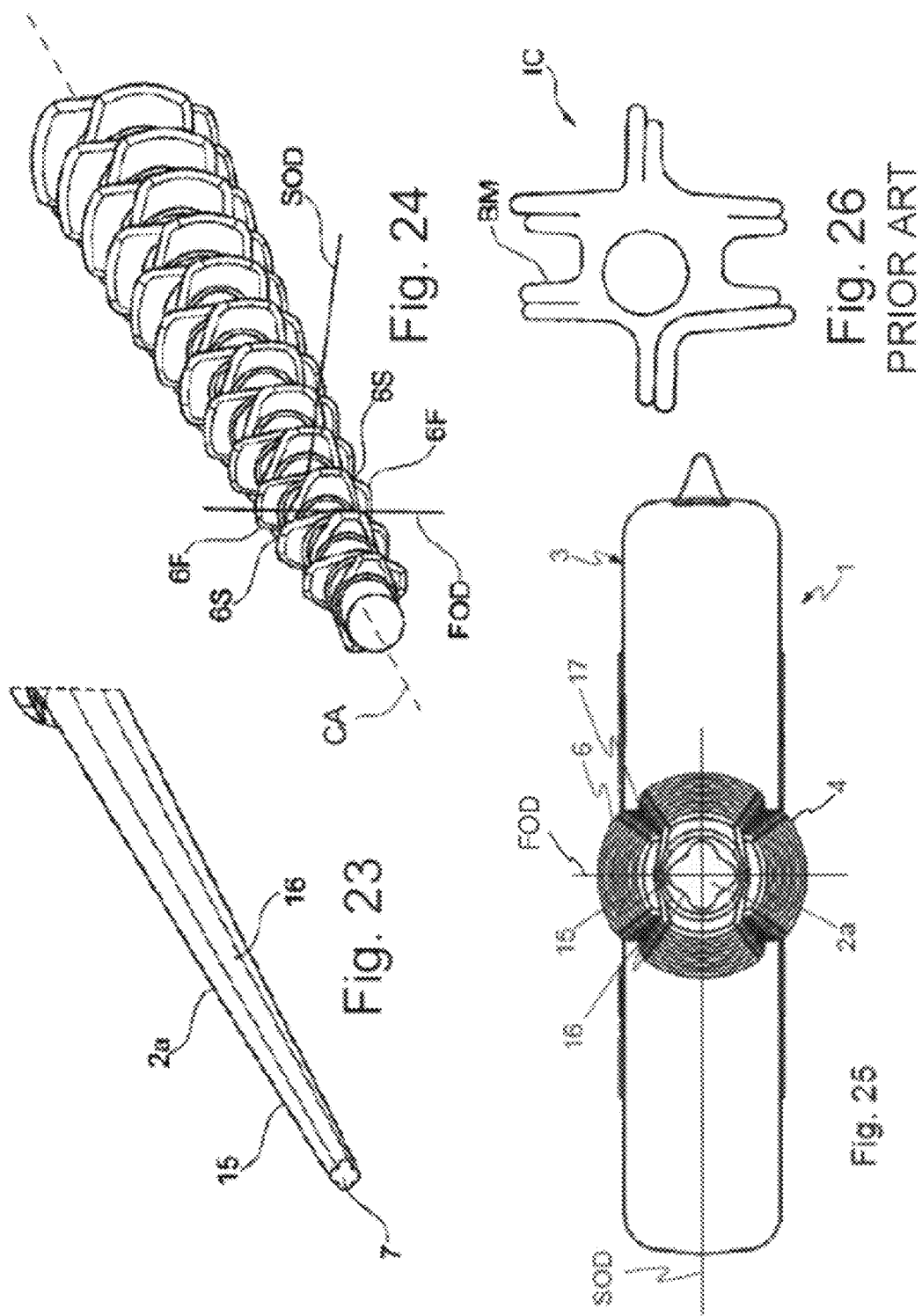

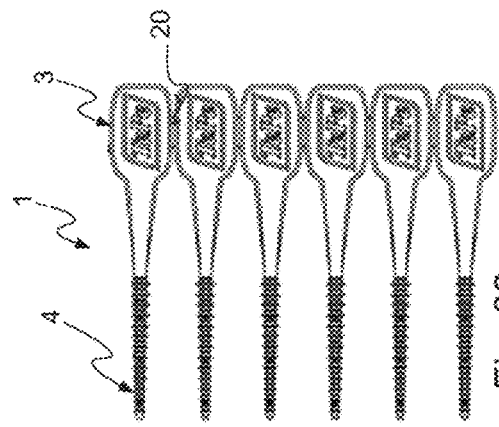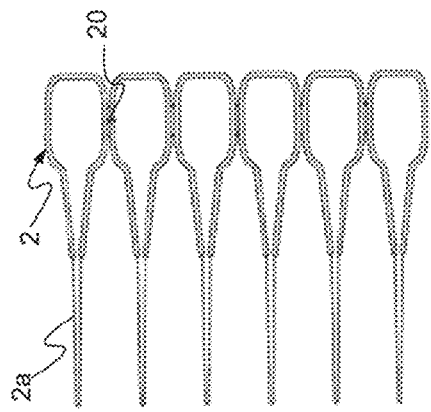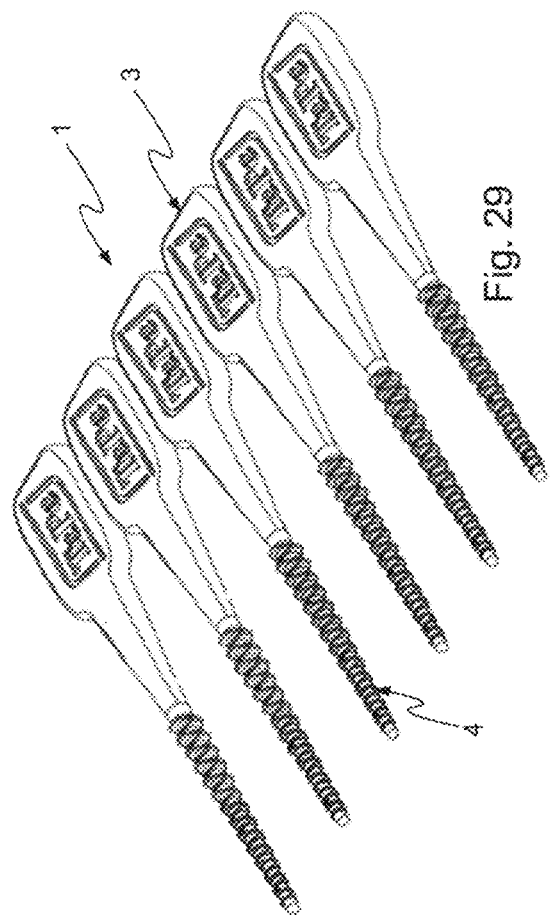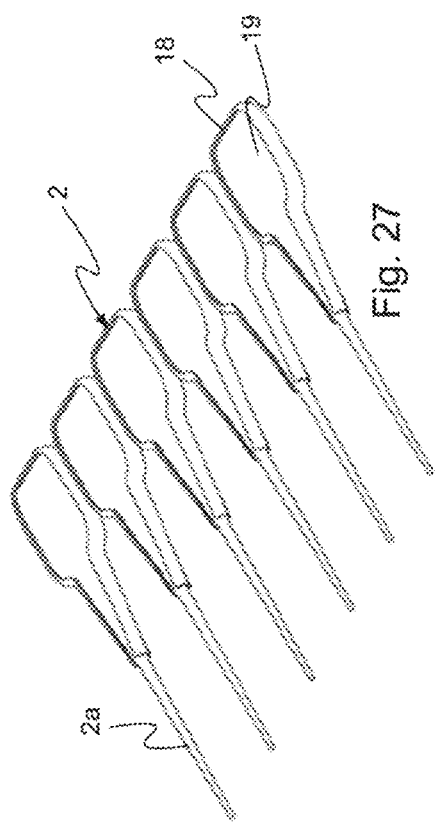

INTERDENTAL CLEANER

PRIORITY CLAIM

This invention claims priority from PCT Application Serial No. PCT/EP2014/078338 filed Dec. 17, 2014, which claims priority to European Application Serial No. 14158195.9 filed Mar. 6, 2014, which is hereby incorporated by reference.

TECHNICAL FIELD

The present invention relates to interdental cleaning devices and in particular to an interdental cleaner having a toothpick design with a brush portion.

BACKGROUND

Various types of interdental cleaners or toothpicks have been used since long ago. Toothpicks of plastic materials are widely used nowadays, and an early example of an interdental toothpick is disclosed in JP-1979-170098U. In one embodiment described therein, the toothpick has a stick-like body of hard synthetic resin which is partially coated by a soft synthetic resin. The soft material portion of the toothpick serves to remove dental plaque and the like from the teeth.

Another example of the same basic structure is shown in U.S. Pat. No. 6,158,444 (corresponding to WO 98/16169), where a rod-like carrier made of hard plastics is partially coated by a soft thermoplastic elastomer (TPE).

Further interdental cleaners of similar type are disclosed in EP-A-153,011 and U.S. Pat. No. 3,775,848 and some recent designs are shown in WO-A-2009/150964, WO-A-2012/156025, WO-A-2013/176297, WO-A-2014/005659, WO-A-2014/023395, WO-A-2014/023424, CN-U-201790907, JP-A-2013188299, JP-A-2013192866 and US-A-2014/0008837.

Certain of the interdental cleaners or toothpicks described in these publications are available on the market, and many of them suffer from different drawbacks which users have experienced. Some toothpicks are of too weak structure which means that they break in use. Other interdental cleaners have inefficient brush portions leading to incomplete cleaning of the teeth. Furthermore, certain toothpicks are uncomfortable to grip and may slip. In summary, many prior-art interdental cleaners are hard to handle by users.

From the above it is understood that there is room for improvements.

SUMMARY

An object of the present invention is to provide a new type of interdental cleaner which is improved over prior art and which eliminates or at least mitigates the drawbacks discussed above.

This object, as well as further objects which will appear from the following description, have now been achieved by an interdental cleaner as defined in appended claim 1 with preferred embodiments set forth in the dependent claims.

In a first aspect, there is provided an interdental cleaner which comprises a gripping portion and a cleaning portion formed by an elongate body made from a thermoplastic material. The cleaning portion has a coating which comprises a heat-vulcanized rubber material and which forms peripheral, flexible brush members. An interdental cleaner of this kind is advantageous since the combination of materials and the heat-vulcanization provides a favourable balance between stiffness and flexibility. The active part of the cleaner contributes to an efficient cleaning process.

In one embodiment, the rubber material comprises a thermoset rubber, preferably a silicone based rubber which has specific favourable properties. The heat vulcanization creates chemical crosslinks in the thermoset rubber which enhances the structure of the interdental cleaner.

Preferably the rubber material has a Shore hardness in the range of 10-60 Shore A, preferably 15-30 Shore A. The thermoplastic material forming the body may be a polyamide or polyester which absorbs humidity from the oral cavity which makes the interdental cleaner more ductile and thereby less vulnerable to break. Preferably, the body is reinforced by glass fiber in a proportion of 5-30% by weight, preferably 10-20% by weight, of the thermoplastic material.

The rubber coating can also be applied at least partially to the gripping portion in order to form a preferred relief structure on the same. This design enhances the gripping comfort and reduces slip. It also opens for promotional use of the interdental cleaner.

The brush members may be formed as peripheral brush flanges which improves the brushing at the teeth surfaces, in particular compared to many prior-art cleaners with thin, radial, pin-like brush members which have only a slight contact with the teeth. Preferably, the outer dimension of the brush flanges is gradually decreasing towards the free end of the cleaning portion, and the outer periphery of the brush flanges preferably forms a substantially circular shape. Hereby an efficient cleaning is achieved since the contact with the teeth is enhanced.

In an embodiment, the brush flanges are spaced substantially equidistant along the cleaning portion and preferably arranged in alternate pairs along the cleaning portion. The first pairs have two brush flanges extending radially from the axis of the cleaning portion in a first opposite direction whereas adjacent second pairs have two brush flanges extending radially from said axis in a second opposite direction. The angle between these directions is about 90°. This design of the active part of the interdental cleaner is beneficial to the cleaning contact with the teeth.

The cleaning portion body is preferably tapering towards the free end of the body which improves the brushing against the teeth surfaces.

Furthermore, the cleaning body portion may be provided with axial grooves and ridges forming a kind of splines. This design improves the adherence of the coating, and it provides a brush flange arrangement with favorable bending properties balanced with appropriate stiffness.

A cleaning portion of this kind has a very slender design which enhances the user's opportunity to efficiently clean the spaces between all teeth in the oral cavity. If the ridges of the cleaning portion body protrude in radial directions, which coincide with the first and second directions of the spaced brush flanges, the advantages are even more manifested.

The gripping portion may have a substantially rectangular cross section defining two opposite, substantially flat gripping surfaces and an outer rim extending along the outer periphery of the gripping portion. Hereby a comfortable gripping is achieved.

Furthermore, the gripping portion may include a transition section which is tapered towards the cleaning portion and which further enhances the gripping.

Preferably, the axial length of the cleaning portion is in the range of 35-55% of the overall axial length of the interdental cleaner, and it is also preferred that the axial length of the gripping portion—including the tapered transition section—is in the range of 45-65% of the overall axial length of the interdental cleaner. By these proportions, an efficient and comfortable teeth cleaning process can be achieved.

In an embodiment, the cross dimension of the cleaning portion at the free end of the interdental cleaner constitutes about 40-50% of the cross dimension of the cleaning portion adjacent to the transition section. This design provides for a slender active part of the interdental cleaner which enhances the user's opportunities to clean all kinds of interdental spaces in the oral cavity.

In a second aspect, an interdental cleaner is suggested which comprises a gripping portion and a cleaning portion formed by an elongate body made from a thermoplastic material. The cleaning portion is provided with a coating with a heat-vulcanized rubber material forming peripheral, flexible brush members. The heat-vulcanized rubber material comprises a thermoset silicone based rubber. This design is favourable, since the durability of the silicone rubber enhances the use of the interdental cleaner.

A third aspect is directed to an interdental cleaner with a gripping portion and a cleaning portion formed by an elongate body made from a thermoplastic material. The cleaning portion has a coating comprising a heat-vulcanized thermoset silicone rubber material and forming peripheral, flexible brush members. The thermoplastic material forming the body is reinforced by fiber material or minerals. By this design, the interdental cleaner is given a favorable balance between stiffness and flexibility which facilitates the cleaning process.

In a fourth aspect, an interdental cleaner is proposed which comprises a gripping portion and a cleaning portion formed by an elongate body made from a thermoplastic material The cleaning portion has a coating which comprises a heat-vulcanized rubber material and which forms peripheral, flexible brush members in the shape of peripheral brush flanges. The outer dimension of the brush flanges is gradually decreasing towards the free end of the cleaning portion, and the outer periphery of the brush flanges forms a substantially circular shape. Advantages are obtained by this design in that the brushing contact with the teeth is improved.

A fifth aspect is directed to an interdental cleaner with a gripping portion and a cleaning portion formed by an elongate body made from a thermoplastic material. The cleaning portion is provided with a coating which comprises a heat-vulcanized rubber material and which forms peripheral, flexible brush members. Furthermore, the cleaning body portion tapers towards the free end of the same and it is provided with axial ridges and grooves. The brush members are formed as peripheral brush flanges, the outer dimension of which is gradually decreasing towards the free end of the cleaning portion and also forming a substantially circular shape. In this aspect, the brush flanges are spaced substantially equidistant along the cleaning portion and are arranged in alternate pairs along the same. The first pairs have two brush flanges extending radially from the axis of the cleaning portion in a first opposite direction and adjacent second pairs have two brush flanges extending radially from the axis in a second opposite direction. The angle between these directions is about 90°, and the ridges of the cleaning body portion protrude in radial directions which coincide with the first and second directions of the brush flanges. This design is advantageous since the arrangement of the brush flanges results in efficient brushing. In particular, the cleaning portion can flex in certain directions.

BRIEF DESCRIPTION OF THE DRAWING

Embodiments of the invention will be described in the following; references being made to the appended diagrammic drawings which illustrate non-limiting examples of how the inventive concept can be reduced into practice.

FIG. 1 is a perspective view of an interdental cleaner of an embodiment of the invention.

FIG. 2 is a front view of the interdental cleaner.

FIG. 3 is a side view of the interdental cleaner.

FIG. 4 is a cross section on a larger scale along the line IV-IV in FIG. 2.

FIG. 5 is an axial, sectional perspective view of the interdental cleaner of FIGS. 1-4.

FIG. 6 is a sectional side view of the interdental cleaner of FIG. 5.

FIG. 7 shows the detail of FIG. 6 on a larger scale.

FIG. 8 is a plan view of an interdental cleaner of a basic size.

FIGS. 9-11 show sections along the lines IX-IX, X-X and XI-XI in FIG. 8.

FIG. 12 is an end view XII-XII of the interdental cleaner of FIG. 8.

FIG. 13 shows the detail of FIG. 12 on a larger scale.

FIG. 14 is a plan view of an interdental cleaner of a slightly larger size than in FIG. 8.

FIGS. 15-17 show sections along the lines XV-XV, XVI-XVI and XVII-XVII in FIG. 14.

FIG. 18 is an end view XVIII-XVIII of the interdental cleaner of FIG. 14.

FIG. 19 shows the detail of FIG. 18 on a larger scale.

FIG. 20 is a sectional side view of the interdental cleaner of FIG. 8.

FIG. 21 is a section along line XXI-XXI of FIG. 20.

FIG. 22 is a corresponding section of the interdental cleaner of FIG. 14.

FIG. 23 is a perspective view of a substrate cleaning portion of the interdental cleaner.

FIG. 24 is a corresponding perspective view of the complete cleaning portion.

FIG. 25 is an end view of the interdental cleaner with a tip cut away for illustration.

FIG. 26 shows a cross section of a prior-art interdental cleaner for comparison.

FIG. 27 is a perspective view of a set of substrates for production of interdental cleaners.

FIG. 28 is a plan view of the set shown in FIG. 27.

FIG. 29 is a perspective view of a set of complete interdental cleaners.

FIG. 30 is a plan view of the set shown in FIG. 29.

DETAILED DESCRIPTION OF THE EMBODIMENTS

Figure 31:
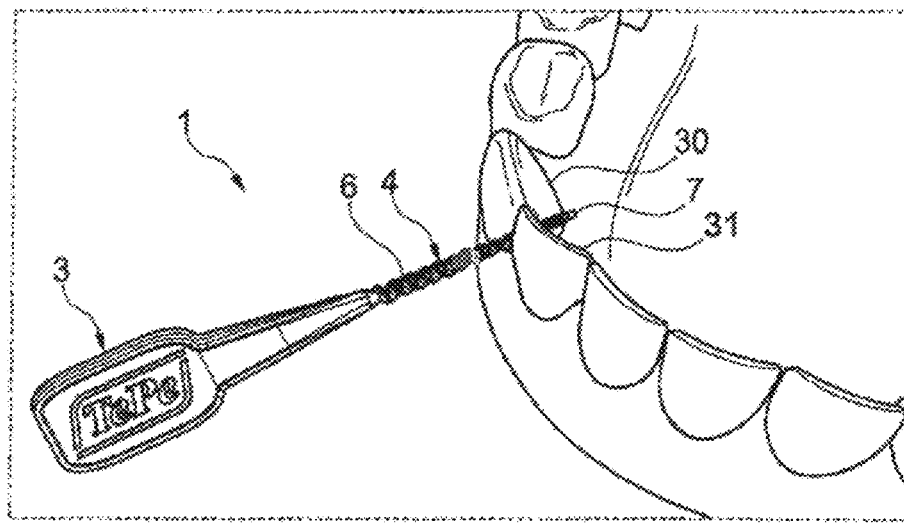
FIG. 31 illustrates how the cleaning portion of an interdental cleaner of FIG. 8 is cleaning a gap between two front teeth.

An interdental cleaner or toothpick 1 according to an embodiment of the invention is shown in FIGS. 1-6, and it is formed by an elongate substrate or body 2 also referred to as carrier in the following. A set of bodies 2 for forming the toothpicks 1 is shown in FIGS. 27-28. The bodies 2 are made of a thermoplastic material, for instance amide plastics, preferably polyamide "6" or alternatively polyester, providing a favorable stiffness for the interdental cleaner 1. Preferably, the pick body 2 is reinforced by glass fiber.

The toothpick 1 has a handle or gripping portion 3, a cleaning portion 4 and an intermediate transition section 5 tapering towards the cleaning portion 4. The cleaning portion 4 is provided with a coating C consisting of a self-adhesive, heat-vulcanized rubber material, preferably a thermoset rubber, such as a liquid, self-adhesive silicone rubber. The coating C forms peripheral, flexible brush members in the shape of brush flanges 6, the outer dimension or radial extension of which is gradually decreasing towards the free end or tip 7 of the cleaning portion 4. The cleaning brush flanges 6 are spaced at the same distance from each other (equidistant) along the cleaning portion 4.

The transition section 5 enhances the user's gripping of the toothpick 1 since he/she can put his/her fingers on this section 5 when performing the reciprocal cleaning movement. Furthermore, the transition section 5 improves the stiffness and thereby the strength of the toothpick 1. The transition between the handle/grip and the elongate brush portion is oftentimes a weak point of prior-art interdental cleaners.

The radial extension of the brush flanges 6 is best shown in the sections in FIGS. 20-21, where the flange 6a closest to the gripping portion 3 has the largest radial projection whereas the flange 6b closest to the tip 7 of the cleaning portion 4 has the smallest radial projection.

As is best shown in FIG. 24, the equidistant brush flanges 6 are arranged in alternate pairs along the cleaning portion 4. The first pairs have two opposite flanges 6F extending radially from the center axis CA of the cleaning portion 4 in a first opposite direction FOD and the second pairs have two opposite flanges 6S extending radially from the center axis CA in a second opposite direction SOD.

Preferably, the angle between these two directions FOD and SOD is about 90° forming a four-wing design of the cleaning portion 4; see FIGS. 13 and 19. The four-wing design can also be described as a four-leaf clover shape seen from the tip 7 of the toothpick 1. The cross-like arrangement of the equidistantly spaced brush flanges 6 provides for a very efficient cleaning of the space between two teeth, that is when the active cleaning part 4 of the toothpick 1 is pushed in a reciprocal movement in this space.

The coating material C is applied also to the gripping portion 3, as can be seen in FIG. 4. The flexible, silicone based material C forms a relief structure on two opposite, substantially flat gripping surfaces 3a and 3b of the gripping portion 3. The relief structure is of so called negative type, which means that coating material C is left out in certain areas so that the surface of the underlying substrate 2 is exposed. Thereby, grooves 8-13 are formed in the coating material C on the gripping portion 3, which form the relief structure.

Since the substrate 2 preferably is of light colour, for instance white, and the coating material C preferably is of a dark colour (cf. FIGS. 8 and 14), the relief structure has a very clear appearance which is favorable for promotional purposes, like exposing trademarks, logotypes, etc (like TePe®).

Furthermore, the relief structure is advantageous in that it provides for a secure gripping of the toothpick 1 at the gripping portion 3. As shown in FIG. 4, the gripping portion 4 has a substantially rectangular cross section forming the two opposite gripping surfaces 3a, 3b provided with the relief structure. Preferably, these two surfaces 3a, 3b are somewhat curved inwards towards the axis of the toothpick 1 so that two opposite concave areas are formed. This concave design, which appears like an oval shape in FIG. 2, further enhances the user's gripping of the toothpick 1.

FIGS. 8-13 and FIGS. 14-19, respectively, show two slightly different sizes of the interdental cleaner 1, 1' according to the general design described above. The cleaning portion 4 of the toothpick 1 of FIG. 8 has a slightly smaller diameter or cross section than the cleaning portion 4' of the toothpick 1' of FIG. 14. Toothpicks 1 can be delivered in various sizes and colours depending on the requirements of the users.

In addition to the relief structure of the gripping portion 3, 3' the toothpicks 1 of FIG. 8 and FIG. 14 are provided with additional relief areas 14, 14' on opposite sides of the transition sections 5, 5'. These relief areas 14, 14' further promote a comfortable gripping of the toothpicks 1, 1' since the user can put his/her finger tip in the small recess formed by the relief area 14, 14'. As described above, the relief area 14, 14' is formed by exclusion of the coating material C so that the surface of the underlying carrier or substrate 2 is exposed.

In FIG. 23 the part 2a of the elongate body 2 which will form the cleaning portion 4 is shown before coating. This cleaning portion body 2a is tapering towards the tip 7 and it has axial ridges 15 and grooves 16 forming splines. These axial splines 15, 16 form a cross-like, four-wing or four-clover cross section which—after coating—matches the four-wing design of the brush flanges 6, as is shown in FIG. 25 where the coated tip is cut away for illustration purposes. The splines design 15, 16 enhances the adherence of the coating material C on the cleaning body part 2a and it matches the brush flange arrangement so that favorable bending properties balanced with appropriate stiffness are achieved.

The axial planes containing the opposite directions FOD and SOD shown in FIG. 24 coincide with the radially projecting ridges 15 of the cleaning body 2a, whereas the radial grooves 16 coincide with sloping recesses 17 formed by the brush flanges 6. This cross-like design of the cleaning portion 4 is favourable since it enhances bending of the active brush part of the toothpick 1 in the directions of the longitudinal recesses 17 along the cleaning portion 4. It is preferred that the cleaning portion 4 can be bent up to 180° with respect to the gripping portion 3.

As is clear from FIG. 25, the angle between two crossing planes including the FOD and SOD forms 90°, whereas the recesses 17 are inbetween (45°) between these planes. The cross-like design is further illustrated in FIGS. 12-13 and 18-19, respectively.

A cross section of a prior-type of interdental cleaner IC is shown in FIG. 26 for comparison with the cross-like design shown in FIG. 25. The known cleaner IC has only a few thin projecting brush members BM with large spaces inbetween. This means that only the tips of the brush members BM take active part in the cleaning process. Contrary to this existing technique, the brush flanges 6 of the interdental cleaner 1 shown in FIG. 25 define an outer periphery which forms a substantially circular shape. This means that the contact surface between the outer edges of the brush flanges 6 is much larger for the toothpicks 1, 1' described herein. Therefore, the cleaning process performed by these toothpicks 1, 1' is improved over prior art.

Certain proportions of the interdental cleaner 1 have been found favourable. In FIG. 3 the axial lengths of the cleaning portion 4 and the gripping portion 3 (including the transition section 5) are shown as L1 and L2. In order to have an efficient active part, that is the cleaning portion 4, the axial length L1 thereof should be in the range 35-55% of the overall length L1+L2 of the toothpick 1. Preferably, this proportion is in the range of 40-50% and most preferred about 45%. Toothpicks 1 produced with these proportions, make it possible for the user to perform an extended reciprocal cleaning movement; thereby taking full advantage of the improved cleaning portion 4.

Furthermore, comfortable gripping of the toothpick 1 is achieved if the axial length (L2) of the gripping portion 4—including the axial length L3 of the transition section 5—is in the range 45-65% of the overall axial length of the toothpick 1. Preferably, this proportion is in the range of 50-60%, and most preferred about 55%.

The design of the active part of the interdental cleaner 1, 1' is slender, as can be seen in FIGS. 21-22. The cross dimension or diameter D2, D2' of the cleaning portion 4 at the tip 7, 7' constitutes about 45% of the cross dimension or diameter D1, D1' of the cleaning portion 4 adjacent to the transition section 5, 5'. The smooth tapering of the body portion 2a makes it possible for the user to reach behind teeth and to push the toothpick 1, 1' into all interdental spaces when cleaning the teeth. The slenderness can of course vary to some extent, and the proportion between the diameters mentioned above can be within the range 40-50% with very efficient result.

Returning now to the materials used, the toothpick body 2 is made from a thermoplastic material, preferably a polyamide, for instance of the type polyamide "6", or PBT (polybutylene terephtalate). In preferred embodiments, the body 2 is reinforced by a reinforcement material. When glass fiber reinforcement is used, favourable properties—such as suitable stiffness—have been achieved if the glass fiber proportion of the toothpick body 2 is within the range 5-30% by weight, preferably 10-20% by weight and most preferred 15% by weight of the thermoplastic material. Certain designs of the interdental cleaner 1 with a glass fiber proportion of less than 12% by weight, in particular 5-10% by weight, have been tested in practice with favourable results.

Other types of reinforcements like carbon and aramide fibers or minerals are feasible, as well as mixtures thereof.

The preferred coating material C for the active part—that is the cleaning portion 4—is a self-adhesive, liquid, heat-vulcanized silicone rubber which has proven good results in practical tests. This thermoset silicone based rubber material has favourable chemical properties. In the heat vulcanization process, chemical crosslinks are created as covalent bonds which cannot be broken by thermodynamic means. Preferably, the heat vulcanization is performed at a temperature of about 120-200° C.

Contrary to the rubber material described above, most prior-art interdental cleaners have an active part or coating consisting of a thermoplastic elastomer (TPE) with physical crosslinks which form weak bonds. When the thermoplastic elastomer is heated, the bonds are broken which means that the polymer chains can move so that the material can be processed again. When cooling the thermoplastic elastomer, the physical crosslinks are formed again.

The chemical crosslinking of the silicone material used in the embodiments described herein gives the active part of the interdental cleaner 1, 1'—that is the coating of silicone rubber—an improved tear strength compared to prior-art cleaners.

In order to obtain favorable flexibility of the interdental cleaner 1, 1' and a comfortable cleaning process using the same, various hardness properties have been tested. The thermoset silicone based rubber material has proven most favorable properties if the Shore hardness is in the range of 10-60 Shore A, preferably 15-30 Shore A and most preferred about 20 Shore A. Practical tests with this silicone rubber material also showed favourable tear-off properties.

Briefly, the process of manufacturing an interdental cleaner of the type described above can be performed as follows. Thermoplastic granules are fed into and melted in a heated injection unit. The melt is then injected into the cold mold, in which it hardens and is shaped in accordance with the cavities of the molding tool. The liquid silicone rubber (LSR) is delivered as two components: a first component A and a second component B. One of the components contains a catalyst whereas the other component contains a cross-linker. The silicone is not created until the two components are mixed. In room temperature, it takes weeks until the silicone is created whereas at higher temperatures the silicone is created in a few seconds (depending on the thickness of the article).

The proportion of the components A and B is 1:1 and they are mixed and injected into a heated molding tool. In the heated tool, a chemical reaction is initiated which is called heat vulcanization—during which the self-adhesive silicone rubber is created.

Thus, the plastic bodies or carriers are injection molded in the cold part of the tool. Thereafter, the bodies/carriers are moved to the heated cavities in which they are overmolded with the silicone rubber material forming the aimed-at coating of the complete toothpicks.

The silicone material is a thermoset rubber which has proven to be very useful for this kind of manufacturing process and which has the aimed-at properties of the interdental cleaner, in terms of adhesion to the substrate of the toothpick, efficient cleaning, suitable flexibility and comfortable gripping and use. Preferable materials for the substrate to which the coating is applied are polyamides, in particular polyamide type "6". As mentioned above, other substrate materials are feasible, for instance PBT.

Before the coating C is applied, a number of bodies 2 are arranged in sets, as is illustrated in FIGS. 27-28. From these figures, it can be seen that the gripping portion has an outer rim 18 which extends along the periphery of the same. This rim 18 defines a kind of recess 19 where the coating C is to be applied in the manufacturing process. The rim 19 contributes to a comfortable gripping of the complete coated toothpick 1. The substrates 2 are connected to each other by thin tear-off bridges or links 20 consisting of the body material.

The links 20 are maintained in the manufacturing process and keep together the finished toothpicks 1 in sets of the type illustrated in FIGS. 29-30. When a toothpick 1 is to be used, the user simply breaks the link 20 between two adjacent toothpicks 1 and separates the toothpick 1 to be used.

With reference to FIG. 31, an interdental cleaner 1 of the type shown in FIG. 8 is illustrated in an initial cleaning position. Thanks to the design of the tapering cleaning portion 4 and a well-balanced reinforcement of the same, a suitable stiffness is achieved which facilitates the axially reciprocating cleaning movement in the gap between two front teeth 30, 31. The splines 15, 16 shown in FIG. 23 also contribute to the suitable stiffness. The flat rectangular gripping portion 3 provides for a secure grip by the fingers of the user so that he/she can perform an efficient cleaning. The ingenious arrangement of the alternating brush flanges 6 of the cleaning portion 4 further enhances the cleaning. The brush flanges 6 are in tight contact with the teeth surface throughout the cleaning process.

Figure 32:
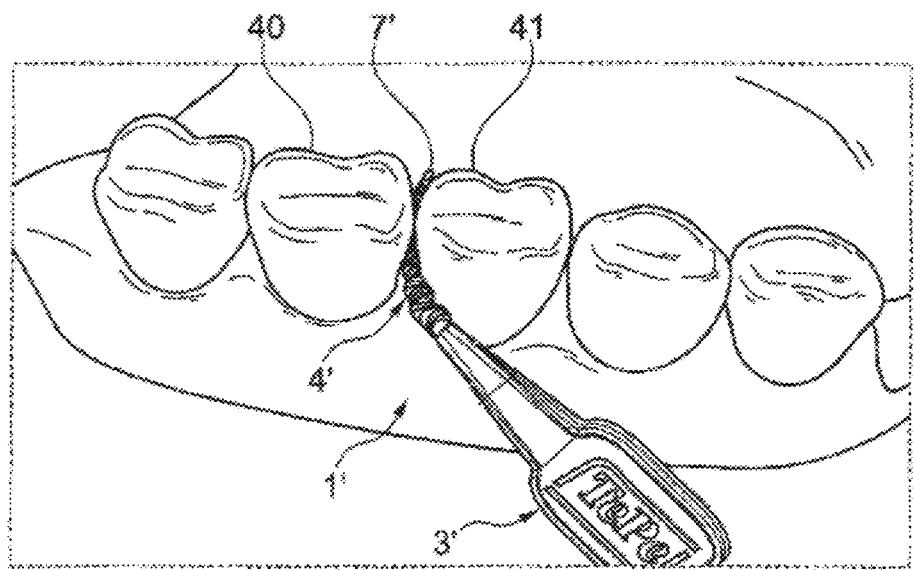
FIG. 32 illustrates how the cleaning portion of an interdental cleaner of FIG. 14 is bent for cleaning a gap between two back teeth.

In FIG. 32 an interdental cleaner 1' of the type shown in 14 is illustrated in a cleaning position where it is bent and partially inserted between two back teeth 40, 41. The balance between stiffness and flexibility of the tapering cleaning portion 4', which can be bent, makes it possible to reach and conveniently clean at locations at the back of the oral cavity. Also in this bent position, the brush flanges 6' are in tight contact with the teeth surfaces so that efficient cleaning is achieved.

Figure 33:
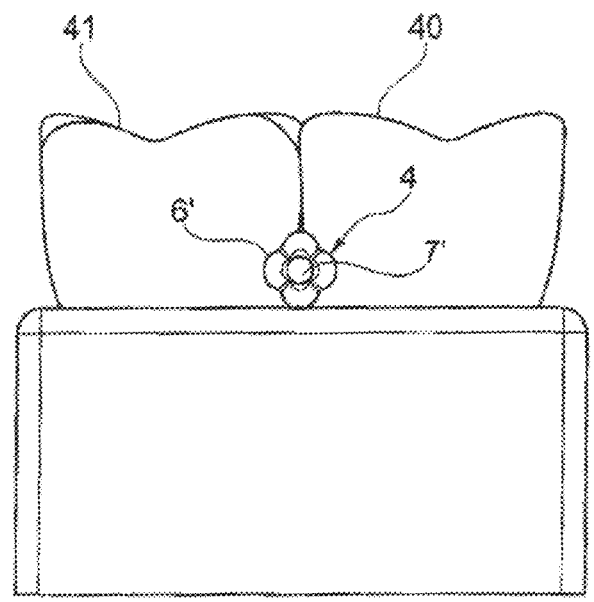
FIG. 33 shows the tip of the cleaning portion of the interdental cleaner of FIG. 32.
Figure 34:
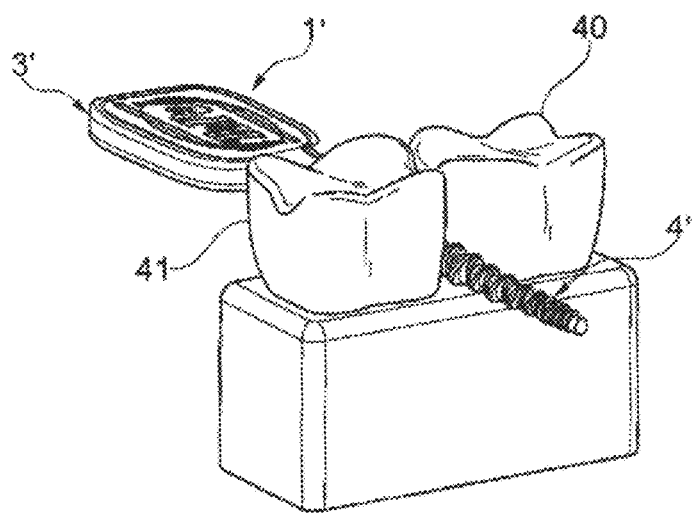
FIG. 34 further illustrates the cleaning action of the interdental cleaner of FIGS. 32-33.
Figure 35:
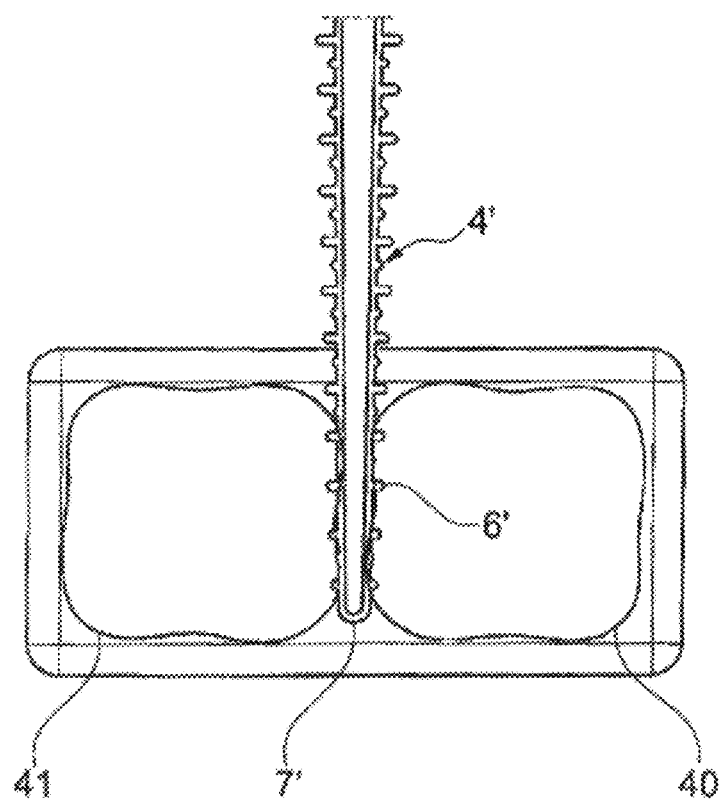
FIG. 35 is a cross section which shows how the cleaning portion of the interdental cleaner of FIGS. 32-34 is inserted in the gap between two back teeth.

The four-wing brush flange arrangement of the interdental cleaner 1' is further illustrated in FIG. 33, whereas in FIG. 34 the interdental cleaner 1' is shown in the perspective. In this position, the flat gripping portion 3' is rotated about 90° compared to the position in FIG. 32. The cleaning process can preferably involve both an axially reciprocating movement and a rotation about the axis of the interdental cleaner 1'.

Finally it should be mentioned that this inventive concept by no means is limited to the embodiments and examples described above, and many modifications are feasible within the spirit and scope of the invention as defined in the appended claims. For instance, specific versions of materials can be used, and the specific design of the toothpicks can vary. Furthermore, the cross-sectional shape of the flanged cleaning portion may be varied depending on specific requirements. In addition to the cross-like design, various star-like designs with several projecting sets of brush flanges can be used. An alternative design is a three-flange design which also provides favourable cleaning contact with the teeth.

The invention claimed is:

1. An interdental cleaner comprising a gripping portion and a cleaning portion, said interdental cleaner being formed by an elongate body, said elongate body being made from a thermoplastic material and said cleaning portion having a coating which comprises a heat-vulcanized rubber material and which forms peripheral, flexible brush members; wherein said elongate body includes a cleaning portion body which, when coated, forms said cleaning portion; wherein said cleaning portion body has a distal end portion and a proximal end portion that is proximal said gripping portion; wherein said cleaning portion body is tapering towards the distal end portion of said cleaning portion body; wherein the brush members include longitudinally spaced apart pairs of brush flanges disposed at longitudinal positions along the elongate body, with each pair of brush flanges including a first brush flange and a second brush flange that is longitudinally aligned with the first brush flange and that is disposed opposite said elongate body from the first brush flange; and wherein only two brush flanges are disposed at one or more of the longitudinal positions along said elongate body.

2. The interdental cleaner as claimed in claim 1, wherein said rubber material comprises thermoset rubber.

3. The interdental cleaner as claimed in claims 1, wherein said rubber material has a Shore hardness in the range of 10-60 Shore A.

4. The interdental cleaner as claimed in claim 1, wherein said thermoplastic material forming the elongate body is reinforced by glass fiber, carbon fiber, aramide fiber or minerals.

5. The interdental cleaner as claimed in claim 4, wherein the fiber reinforcement comprises glass fiber in a proportion of 5-30% by weight.

6. The interdental cleaner as claimed in claim 1, wherein said thermoplastic material comprises amide plastics or polyester.

7. The interdental cleaner as claimed in claim 1, wherein said coating is also applied at least partially to said gripping portion.

8. The interdental cleaner as claimed in claim 7, wherein the coating applied to the gripping portion forms a relief structure on the same.

9. The interdental cleaner as claimed in claim 1, wherein the brush flanges have an outer dimension, and the outer dimension of the brush flanges is gradually decreasing towards the distal end portion of the cleaning portion.

10. The interdental cleaner as claimed in claim 1, wherein the brush flanges have an outer periphery, and the outer periphery of the brush flanges forms a substantially circular shape.

11. The interdental cleaner as claimed in claim 1, wherein the brush flanges are spaced substantially equidistant along the cleaning portion.

12. The interdental cleaner as claimed in claim 1, wherein the brush flanges are arranged in alternate pairs along the cleaning portion, first pairs having two brush flanges extending radially from the axis of the cleaning portion in a first opposite direction and adjacent second pairs having two brush flanges extending radially from said axis in a second opposite direction that is offset from the first direction by a non-zero angle between said first and second directions.

13. The interdental cleaner as claimed in claim 12, wherein said cleaning portion body comprises axial ridges and grooves, and said ridges of the cleaning portion body protrude in radial directions which coincide with said first and second directions of the brush flanges.

14. The interdental cleaner as claimed in claim 1, wherein the gripping portion has an outer periphery, a substantially rectangular cross section defining two opposite, substantially flat gripping surfaces and an outer rim extending along the outer periphery of the gripping portion.

15. The interdental cleaner as claimed in claim 1, wherein the gripping portion comprises a transition section which is tapered towards the cleaning portion.

16. The interdental cleaner as claimed in claim 15, wherein the axial length of the gripping portion including the tapered transition section is in the range of 45-65% of the overall axial length of the interdental cleaner.

17. The interdental cleaner as claimed in claim 16, wherein the cross dimension of the cleaning portion at the distal end portion of said cleaning portion body constitutes about 40-50% of the cross dimension of the cleaning portion adjacent to the transition section.

18. The interdental cleaner as claimed in claim 1, wherein the axial length of the cleaning portion is in the range of 35-55% of the overall axial length of the interdental cleaner.

19. An interdental cleaner comprising a gripping portion and a cleaning portion, said interdental cleaner being formed by an elongate body, said elongate body being made from a first material, said cleaning portion being coated by a second material that forms a coating and that is softer than said first material, said coating forming flexible brush flanges protruding from said coated cleaning portion; wherein said elongate body comprises a cleaning portion body which, when coated, forms said cleaning portion; wherein the brush flanges include longitudinally spaced apart pairs of brush flanges disposed at longitudinal positions along said elongate body, with each pair of brush flanges including a first brush flange and a second brush flange that is longitudinally aligned with the first brush flange and that is disposed opposite said elongate body from the first brush flange; and wherein only two brush flanges are disposed at one or more of the longitudinal positions along said elongate body.

20. The interdental cleaner as claimed in claim 19, wherein the first material is a plastic material.

21. The interdental cleaner as claimed in claim 19, wherein the first material is a thermoplastic material.

22. The interdental cleaner as claimed in claim 19, wherein the second material is an elastic material.

23. The interdental cleaner as claimed in claim 19, wherein the second material is a rubber material.

24. An interdental cleaner comprising a gripping portion and a cleaning portion having a longitudinal axis, said interdental cleaner being formed by an elongate body, said elongate body being made from a thermoplastic material and said cleaning portion having a coating which comprises a heat-vulcanized rubber material and which forms peripheral, flexible brush members; wherein the brush members are formed as peripheral brush flanges arranged in alternate pairs along said cleaning portion and disposed at longitudinal positions along said elongate body, with first pairs having two brush flanges extending radially from said longitudinal axis of said cleaning portion in a first opposite direction and adjacent second pairs having two brush flanges extending radially from said longitudinal axis of said cleaning portion in a second opposite direction; and wherein only two brush flanges are disposed at one or more of the longitudinal positions along said elongate body.

25. An interdental cleaner comprising a gripping portion and a cleaning portion, said interdental cleaner being formed by an elongate body, said elongate body being made from a thermoplastic material and said cleaning portion having a coating which comprises a heat-vulcanized thermoset silicone rubber material and which forms peripheral, flexible brush members; wherein said thermoplastic material forming said elongate body is reinforced by fiber material or minerals; wherein the brush members include longitudinally spaced apart pairs of brush flanges disposed at longitudinal positions along said elongate body, with each pair of brush flanges including a first brush flange and a second brush flange that is longitudinally aligned with the first brush flange and that is disposed opposite said elongate body from the first brush flange; and wherein only two brush flanges are disposed at one or more of the longitudinal positions along said elongate body.

26. An interdental cleaner comprising a gripping portion and a cleaning portion, said interdental cleaner being formed by an elongate body, said elongate body being made from a thermoplastic material and said cleaning portion having a coating which comprises a heat-vulcanized rubber material and which forms peripheral, flexible brush members; wherein said brush members are formed as peripheral brush flanges, wherein the brush flanges include longitudinally spaced apart pairs of brush flanges disposed at longitudinal positions along said elongate body, with each pair of brush flanges including a first brush flange and a second brush flange that is longitudinally aligned with the first brush flange and that is disposed opposite said elongate body from the first brush flange, wherein only two brush flanges are disposed at one or more of the longitudinal positions along said elongate body.

27. An interdental cleaner comprising a gripping portion and a cleaning portion having a distal end portion and a proximal end portion that is proximal said gripping portion, said interdental cleaner being formed by an elongate body, said elongate body being made from a thermoplastic material and said cleaning portion having a coating which comprises a heat-vulcanized rubber material and which forms peripheral, flexible brush members; wherein the cleaning portion body is tapering towards the distal end portion of the cleaning portion and comprises axial ridges and grooves; wherein said brush members are formed as peripheral brush flanges; wherein the brush flanges are disposed at longitudinal positions along said elongate body, are spaced substantially equidistant along the cleaning portion and are arranged in alternate pairs along the same, first pairs having two brush flanges extending radially from the axis of the cleaning portion in a first opposite direction and adjacent second pairs having two brush flanges extending radially from said axis in a second opposite direction that is offset from the first direction by a non-zero angle between said first and second directions; wherein only two brush flanges are disposed at one or more of the longitudinal positions along said elongate body.

* * * * *